United States Patent [19]

Miremadi et al.

[11] Patent Number: 5,342,701
[45] Date of Patent: Aug. 30, 1994

[54] TRANSITION METAL OXIDE FILMS AND GAS SENSORS THEREOF

[75] Inventors: Bijan K. Miremadi, Coquitlam; Ravi C. Singh, Surrey; Stanley R. Morrison, Burnaby; Konrad Colbow, West Vancouver, all of Canada

[73] Assignee: 410261 B.C. Ltd., West Vancouver, Canada

[21] Appl. No.: 860,068

[22] Filed: Mar. 30, 1992

[51] Int. Cl.$^5$ ............................................. B32B 9/00
[52] U.S. Cl. ......................... 428/701; 428/411.1; 428/472; 428/689; 428/702; 428/704; 423/53; 423/561.1; 502/220
[58] Field of Search ............... 428/701, 702, 704, 689, 428/472, 336, 411.1, 210; 423/53, 561.1; 502/220

[56] References Cited

U.S. PATENT DOCUMENTS

| 4,822,590 | 4/1989 | Morrison et al. | 423/561.1 |
| 4,853,359 | 8/1989 | Morrison et al. | 502/220 |
| 4,996,108 | 2/1991 | Divigalpitya et al. | 428/411.1 |

FOREIGN PATENT DOCUMENTS 61-118651 of 0000 Japan.

Primary Examiner—Patrick J. Ryan
Assistant Examiner—Abraham Bahta
Attorney, Agent, or Firm—Norman M. Cameron

[57] ABSTRACT

Thick oriented films are produced from oxides of molybdenum, tungsten or titanium. These films comprise a plurality of single-molecular thickness layers of semi-crystalline oxide having parallel basal planes. The oxides are produced by sintering highly oriented films of the corresponding metallic sulfide at a temperature of 300°–350° C. The film may be deposited on a substrate between electrical contacts to function as a gas sensor for hydrogen.

3 Claims, 6 Drawing Sheets ature of 20° C.;

TRANSITION METAL OXIDE FILMS AND GAS SENSORS THEREOF

BACKGROUND OF THE INVENTION

1. Field of the Invention

This invention relates to highly oriented, partially crystalline films of oxides of molybdenum, tungsten and titanium and to sensors for reducing gases such as hydrogen made thereof.

2. Description of Related Art

The production of single molecular thickness layers of $MoS_2$ and other transition metal dichalcogenides is disclosed in U.S. Pat. No. 4,822,590 to S. Roy Morrison et al. The $MoS_2$ is exfoliated into monolayers by intercalation with lithium followed by reaction with water. The reaction between the water and the lithium forces the layers of $MoS_2$ apart into one-molecule-thick platelets. Flocculation occurred rapidly when the pH was reduced to a value of 3 or less.

U.S. Pat. No. 4,996,108 to Divigalpitya et al carries this process further by forming a suspension of a transition metal dichalcogenide in water and adding to the suspension a liquid which is immiscible with water. The mixture is agitated, then allowed to rest. A sheet-like composition of about 500 Å to 750 Å forms at the interface of the water and the immiscible liquid.

In U.S. Pat. No. 4,853,359 to Morrison et al., a novel flocculated, supported single-layered transition metal dichalcogenide catalyst is disclosed. The patent discloses that if the pH is maintained at a value above about 3, the suspension of $MoS_2$ will not flocculate, but will stay for days or more suspended in water. The next step in producing the catalyst according to the patent is to add a catalytic promoter to the suspension. A solid is formed by adding this promoter or support substance to the water. The flocculated solid is then separated from the liquid.

In an Article, J. Appl. Phys. 69(9), 6373 (1991) by Miremadi et al., the deposition of thick oriented films of a transition metal dichalcogenide, with a thickness in the order of 0.1 to 10 microns is disclosed.

In pending U.S. patent application Ser. No. 07/704,432, a novel transition metal dichalcogenide with a house-of-cards (HOC) structure is disclosed and a method for production thereof. The method involves reducing the pH of a suspension of single-molecular thickness platelets of $MoS_2$, or other transition metal dichalcogenides, until they flocculate, and the pH is within a range between a first pH where basal planes of the platelets have a zero charge and a second pH where edges of the platelets have a zero charge.

The use of the semiconductor metal oxides $MoO_3$ or $WO_3$ in gas sensors using thermal evaporation, sputtering and some impregnation techniques is described in the prior art. For example, in Japanese Patent No. 61-118651 to Ayusawa, an evaporated film of $WO_3$ is used as a hydrogen gas sensor. The same patent describes a rather lengthy chemical impregnation process for deposition of polycrystalline $MoO_3$ powder, using binders and adhesives, although the $MoO_3$ data is not presented.

Films made of oxides of molybdenum, tungsten and titanium have been produced on a substrate by sintering highly oriented sulfide films of the same metals. However, this is done at temperatures above 350° C., resulting in highly crystallized films where the particles tend to migrate to form much larger particles. The oxide particles lose the previous high orientation of the sulfide film and sensors prepared therefrom have little or no sensitivity to hydrogen.

Sensors have also been prepared from commercial oxide powders of the same metals or from the sulfide powders of the same metals which have been impregnated with platinum and sintered above 350° C. These sensors show relatively poor sensitivity to hydrogen.

SUMMARY OF THE INVENTION

It is an object of the invention to provide a sensor for reducing gases with a higher sensitivity and selectivity to hydrogen gas.

It is also an object of the invention to provide a hydrogen gas sensor which operates as a relatively low temperature, preferable at 120° C. or lower, to reduce power consumption and the possibility of igniting the gas/air mixture.

It is a further object of the invention to minimize the physical dimensions of the sensor, preferably with a spot-size sensing element less than 1 mm in diameter.

In accordance with these objects, the invention provides a composition having the formula $MO_z$, wherein M is selected from the group consisting of molybdenum, tungsten and titanium, O is oxygen and z is 3 where M is molybdenum or tungsten and 2 where M is titanium. The composition is in the form of a semi-crystalline film comprising a plurality of single molecular thickness layers which are oriented so their basal planes are parallel.

The invention also provides a sensor for reducing agents, such as hydrogen gas, comprising an insulating substrate with a pair of electrical contacts spaced-apart thereon. A film is located on the substrate between the contacts having the composition $MO_z$ wherein M is selected from the group consisting of molybdenum, tungsten and titanium, O is oxygen and z is 3 where M is molybdenum or tungsten and 2 where M is titanium. The film is semi-crystalline and comprises the plurality of singular molecular thickness layers which are oriented so their basal planes are parallel.

The film may be impregnated with a metal selected from the group consisting of palladium, platinum and ruthenium. The film may contain $MS_2$, wherein S is sulfur.

The invention also provides a method of making films and sensors of $MO_z$ by oxidizing films comprising a plurality of single-molecular thickness layers of $MX_2$, wherein X is selected from the group consisting of sulfur and selenium and wherein basal planes of the layers are parallel. The $MX_2$ is preferable oxidized by sintering at a temperature of 300°–350° C.

DESCRIPTION OF THE PREFERRED EMBODIMENTS

Figure 1:
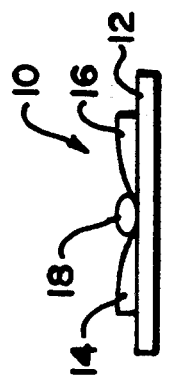
FIG. 1 is a sectional view of a gas sensor according to an embodiment of the invention.

FIG. 1 shows a sensor 10 for reducing agents, such as reducing gases, and hydrogen in particular. It includes a substrate 12 which is of alumina in this embodiment although other electrical insulators could be substituted. There is a pair of space-apart electrical contacts 14 and 16 which are made of gold in this example.

There is a film 18 between contacts. The film is relatively thick in this example, being about 1 micron thick and is about 1 mm in diameter, this being the distance between the contacts. These dimensions are not critical.

The film is highly oriented and is partially crystalline. It may be considered as a plurality of single molecular thickness layers of an oxide of one of the transition metals molybdenum, tungsten or titanium. The layers are arranged with their basal planes parallel to each other.

In brief, when exposed to hydrogen or possibly other reducing gases or agents, the oxide is reduced, thus affecting the conductivity of the film. The conductivity or resistivity of the film is measured after exposure to the reducing agent and compared to the previous conductivity or resistivity. The concentration of the hydrogen or other reducing agent is proportional to the change in conductivity or resistivity. The resistance of the film drops on exposure to hydrogen while its conductivity correspondingly increases. After a reading is obtained, the film must be exposed to air or another source of oxygen to regenerate the oxide prior to reuse of the sensor.

The sensor is prepared starting with a piece of alumina sheet or another suitable substrate. Single layers of a transition metal dichalcogenide are deposited on the substrate. The transition metal may be selected from the group consisting of molybdenum, tungsten and titanium. Their sulfides are typically used although selenium could replace sulfur. Depositing such single layers of transition metals dichalcogenides on substrates is known in the prior art and disclosed in Article, J. Appl. Phys. 69(9), 6373 (1991) by Miremadi et al. and in U.S. Pat. No. 4,996,106 to Divigalpitya et al. In this particular case, the film is deposited on the substrate between the electrical contacts 14 and 16.

A catalyst such as platinum, palladium or ruthenium is deposited and dispered into the thick film. The film is then sintered at a temperature of 300°–350° C. in air for approximately 20–30 minutes. This converts the transition metal dichalcogenide to the corresponding oxide. The catalyst serves two functions. First it helps further oxidation of sulfur and molybdenum during the sintering. With no catalyst the S/Mo ratio drops from 2 to 0.25 during sintering. The ratio drops by a further factor of 3 with the catalyst. The second function is the dissociation of $H_2$ to $2H^+ + 2e^-$ over the surface of the particles matrix.

In this specified temperature range $MoS_2$ or other transition metal dichalcogenide is converted to a beta phase oxide in the form of very fine and uniformly distributed particles. The oxide films prepared in this temperature range are partially crystalline, compared to the alpha phase oxide which forms above 450° C., and remain as highly oriented as its parent single layer dichalcogenide, as shown by x-ray diffraction. The grains of the beta phase are partially attached to each other, providing a better electrical conductivity whereas the grains of the alpha phase are rather detached from one another. The x-ray diffusion pattern of the beta phase shows broad lines while the alpha phase lines are very sharp. In addition to being highly oriented to the substrate surface, the beta phase provides a uniformly distributed and interconnected particle oxide matrix.

The presence of the catalyst on the surface further enhances the oxidation process to the extent that the S/Mo ratio approaches zero as measured by SEM, SAM and laser ablation analysis. Pure $MoS_2$ is only partially oxidized at 300°–350° C. The presence of Pt or other catalysts catalyses the reaction so it occurs at a temperature low enough to avoid re-crystallization, thus producing the fine uniform particle size.

The catalyst particles are highly dispersed between the transition metal atoms due to formation of strong bonds between the catalyst and the transition metal. As a result, the platinum or other catalyst atoms donate electrons to the Mo or other transition metal. The original conductance of the film is thus increased by a factor of about 10 compared to the same film produced without the Pt deposition. Conversely, the sintered films with no Pt have a resistance of 100 Megohms, but with the Pt the resistance to about 10 Megohms.

The sintering temperature is critical. Films sintered at temperatures above 350° C. are highly crystallized and particles tend to migrate to form much larger particles. As mentioned previously, sensors produced in this manner have little or no sensitivity to hydrogen. In general and under similar experimental conditions the sensitivity of $MoS_2$ based sensor is much higher than the $WS_2$ based sensor which is superior to that of the $TiS_2$ based sensor.

A comparison of the Pt, Pd and Ru deposited sensors at 120° C. and a hydrogen concentration of 275 ppm indicated that the Pd deposited sensor had a faster response time compared to the Pt deposited sensor and Pt was similarly faster than the Ru deposited sensor.

Preliminary testing has shown that almost no sulfide remains in the films after sintering with catalyst present. However, some quantities of sulfide likely remain in trace amounts at least in some examples. At this stage it is believed that the remaining traces of sulfide, if any, have no effect on the function of the sensor. A good example is the films made from restacked $MoS_2$ single layers after the deposition of the catalyst. These films have more retained sulfur but have almost no sensitivity to hydrogen detection. This once again shows that it is the structural effect of the matrix of oxide particles which is responsible for hydrogen detection and not the individual oxides or sulfide grains. It has not been conclusively established what role if any such remaining traces of sulfide might have on the function of the sensor.

EXAMPLE 1

The thick oriented films were prepared by the method of exfoliation by steps A–D below:

Step A: The layered sulfide powders described above were exposed to n-butyllithium in hexane in an inert atmosphere. This results in the lithium metal being intercalated between the sulfide layers. The sulfide is then immersed in water. The resulting reaction produces hydrogen gas which expands and separates the powder into single layers in a suspension of pH 12 due to the LiOH formed.

At this pH, the single layers are charged negatively due to the OH⁻ ions at the surface, so the layers repel each other and remain suspended in water several days. The concentration of the suspension at this stage is about 1 g/100 ml.

The intercalation of lithium can also be achieved using lithium vapor at approximately 500° C. in an encapsulated capsule as described in the related art described above.

Step B: Using diluted nitric acid (about 1 liter in volume) the pH of the resulting suspension in Step A (about 1 g/100 ml) is lowered immediately after the exfoliation to the pH of the corresponding point of zero charge (in the case $MoS_2$, the pH is 2±0.2). At this pH the material flocculates in a form that basal planes are positive, but the edges are negative, so that the edges are attracted to the basal planes and form a new structure resembling the house of cards structure. The corresponding pH for $WS_2$ is pH 1±0.2 and for $TiS_2$ it is pH 2.5±0.2.

Step C: The liquor from Step B was decanted and the pH was raised to a pH 3–4 using distilled water (pH=5). The layers then redisperse, forming a very stable suspension against the flocculation for several weeks.

Step D: 10 microliters of the suspension prepared in Step C, with a $MoS_2$ concentration of about 2 mg/ml, was then deposited on the substrate. Immediately after, the layers tend to orient themselves to the plane of the substrate, such that the basal planes are substantially parallel to the surface of the substrate. This is particularly true when the substrate is made of a polar material. A highly oriented thick film forms with the thickness depending upon the concentration of single layer material in the suspension. With a concentration of about 2 mg/ml the thickness is about 1 micron. The deposited films were then dried at room temperature.

Step E: About 10 microliters from a 0.015 mole solution of platinum chloride was spread over the surface of the film and dried at room temperature. The solution spread quickly with the film providing a high dispersion of Pt.

Step F: The deposited films prepared above were then transferred to a furnace and sintered in air at 300°–350° C.

It was noted that if Step B above is by-passed, and the pH 12 is lowered directly to pH 3–4, the material flocculates and restacks in a randomly oriented form, resulting in a disoriented powder. Sensors produced from this material show very little sensitivity to even high concentrations of hydrogen gas at 120° C.

EXAMPLE 2

In this example the films are prepared somewhat differently, but equivalent to the steps in Example 1.

Step A: Suspension of pH 12 single-layered material is prepared as in Step A of Example 1.

Step B: The suspension of Step A is washed with distilled water (pH=5) and centrifuged for 30 minutes at 2500 rpm.

Step C: Step B repeated for a second time.

Step D: The pH was lowered to pH 2.2±0.2 using dilute nitric acid.

Step F: The pH was increased to pH 3–4 using distilled water.

Step G: The $MoS_2$ was transferred to the substrate as in Step D of Example 1.

Step H: Platinum chloride was deposited as in Step E of Example 1.

Step I: The films were sintered as in Step F of Example 1.

OPERATION OF THE SENSOR

The sensor 10 can be operated at room temperature and up to an elevated temperature of about 200° C. depending upon the response time desired. The response time decreases with increasing temperature. Above 200° C. there is a decrease of sensitivity to hydrogen.

Figure 3:
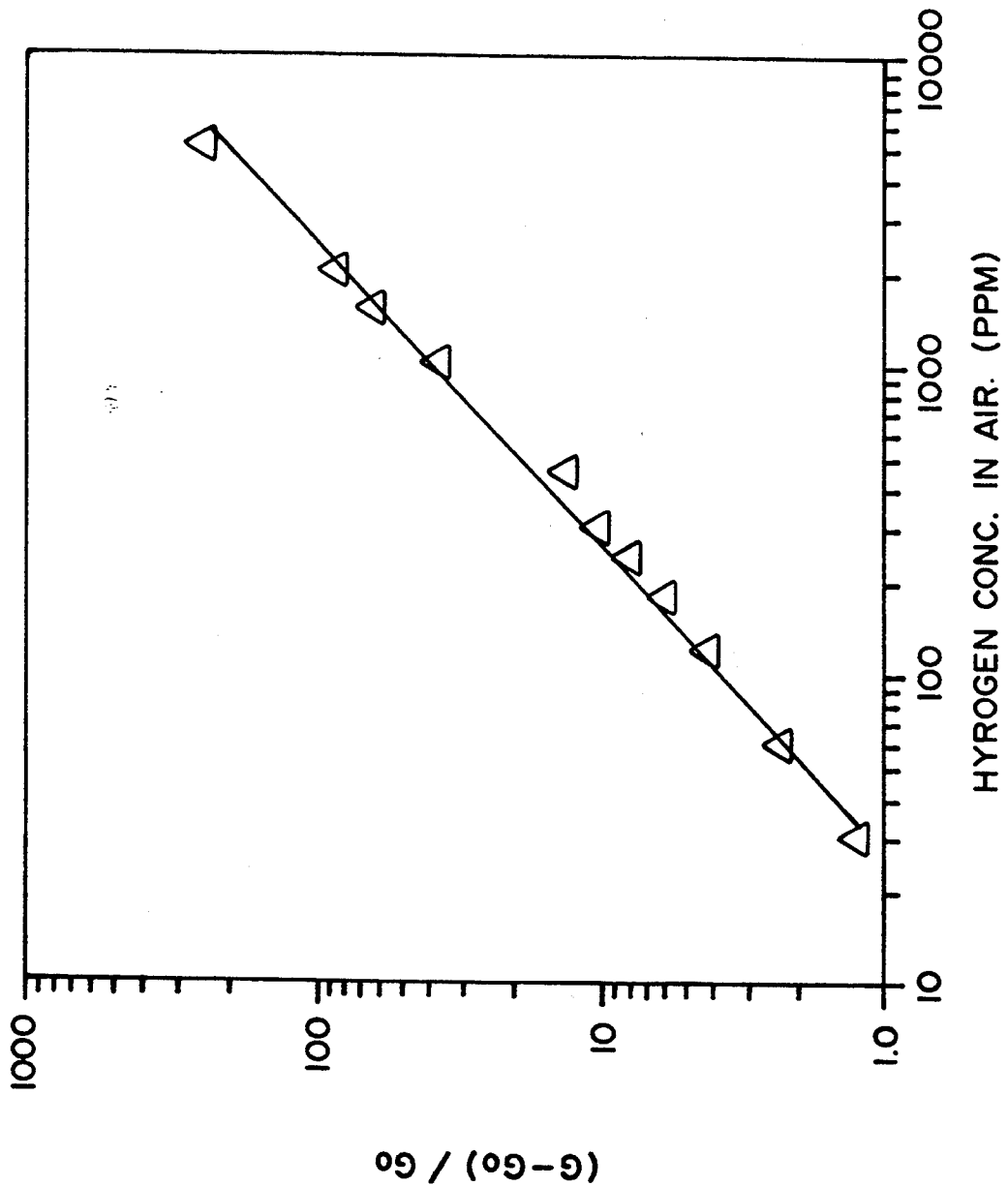
FIG. 3 is a graph showing the sensitivity of the sensor for different concentrations of hydrogen gas in air, at 120° C.
Figure 2:
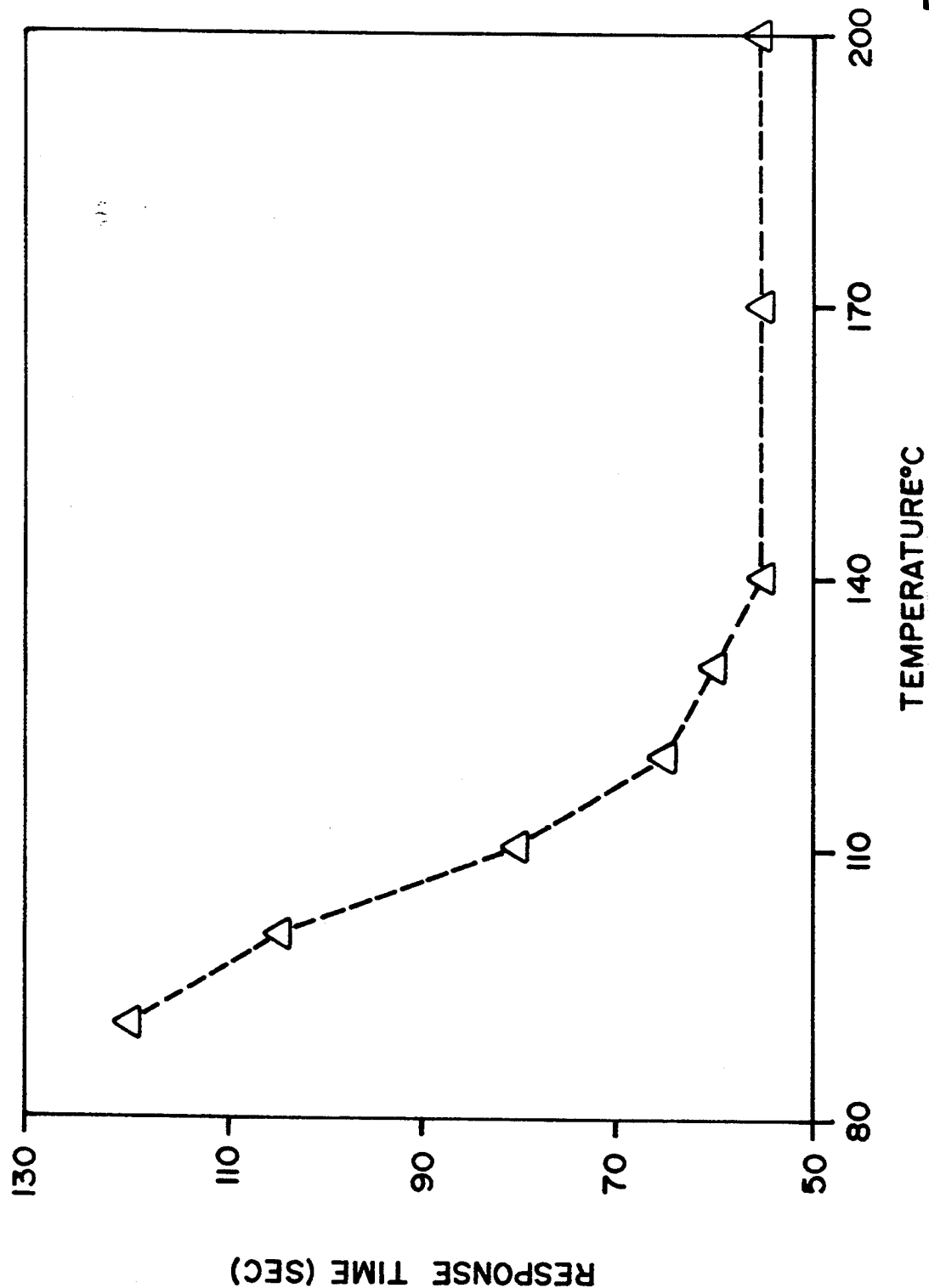
FIG. 2 is a graph showing the response time of the sensor for a range of operating temperatures.
Figure 4:
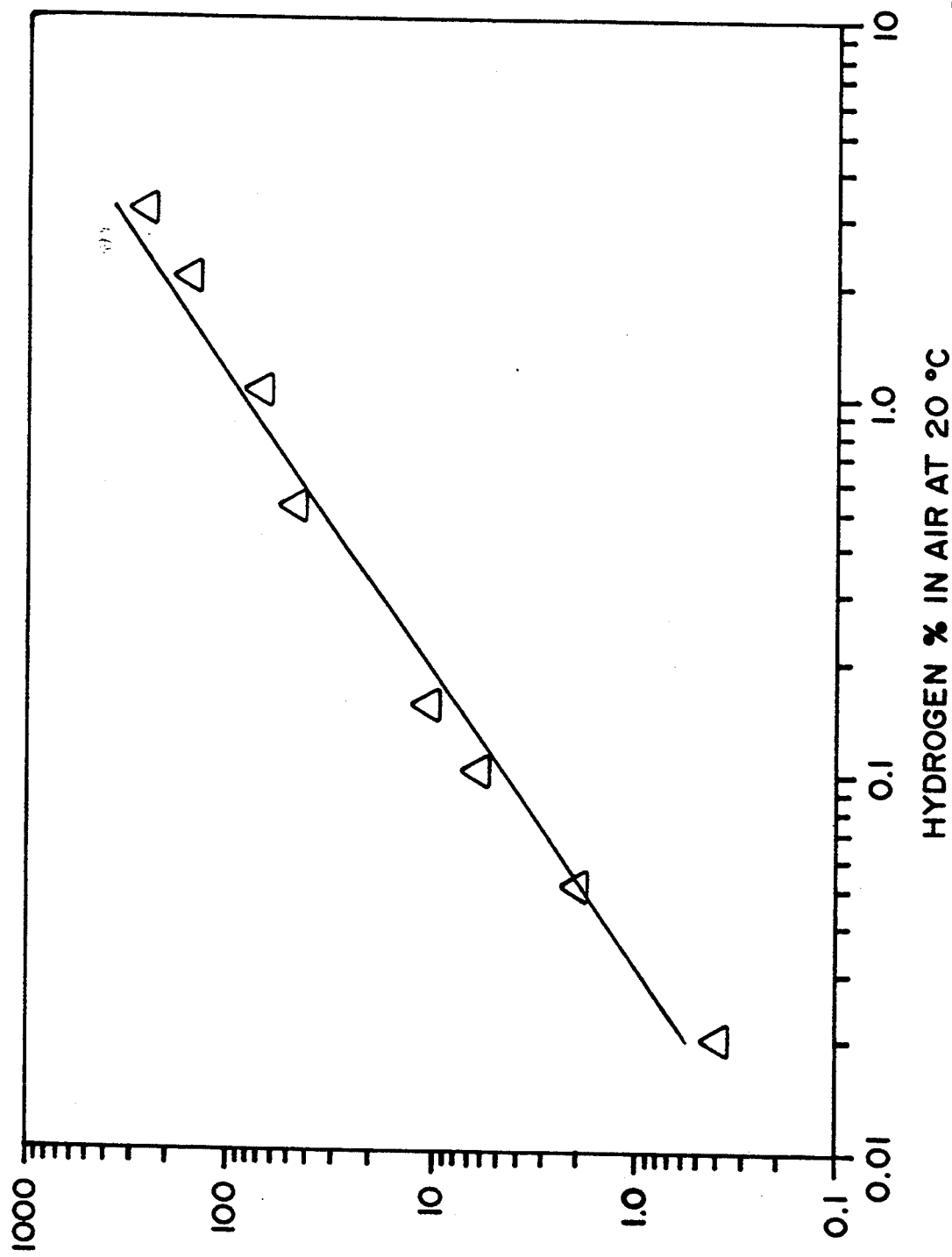
FIG. 4 is a graph showing the sensitivity of the sensor for different concentrations of the gas and air at a temperature of 20° C.

Referring to FIG. 3, the sensitivity of the sensor is expressed as $(G-G_0)/G_0$, where G is the conductivity of the sensor in the presence of hydrogen while $G_0$ is its conductivity without hydrogen present. The sensitivity factor of the sensor is plotted against the concentration of hydrogen gas at 120° C. in air. The sensor shows high linearity in the range of 30 ppm to about $10^4$ ppm (1%) hydrogen as seen in FIG. 2. The response time of the sensor at 120° C. is about 1 minute.

At 20° C. (room temperature) the sensitivity factor of the sensor is linear in the range of 100 ppm to $5\times10^4$ ppm (5%). However, the response time is about 8 minutes and requires electronic circuits to decrease the rise time.

FIG. 2 shows the response time of the sensor for hydrogen at a concentration of 275 ppm. At higher concentrations of 1% to 5% the response to hydrogen is also linear but has a different slope than for concentrations less that 1% hydrogen. FIG. 3 shows the sensitivity factor for a Mo based gas sensor against the concentration of hydrogen gas at 120° C. in air.

Figure 5:
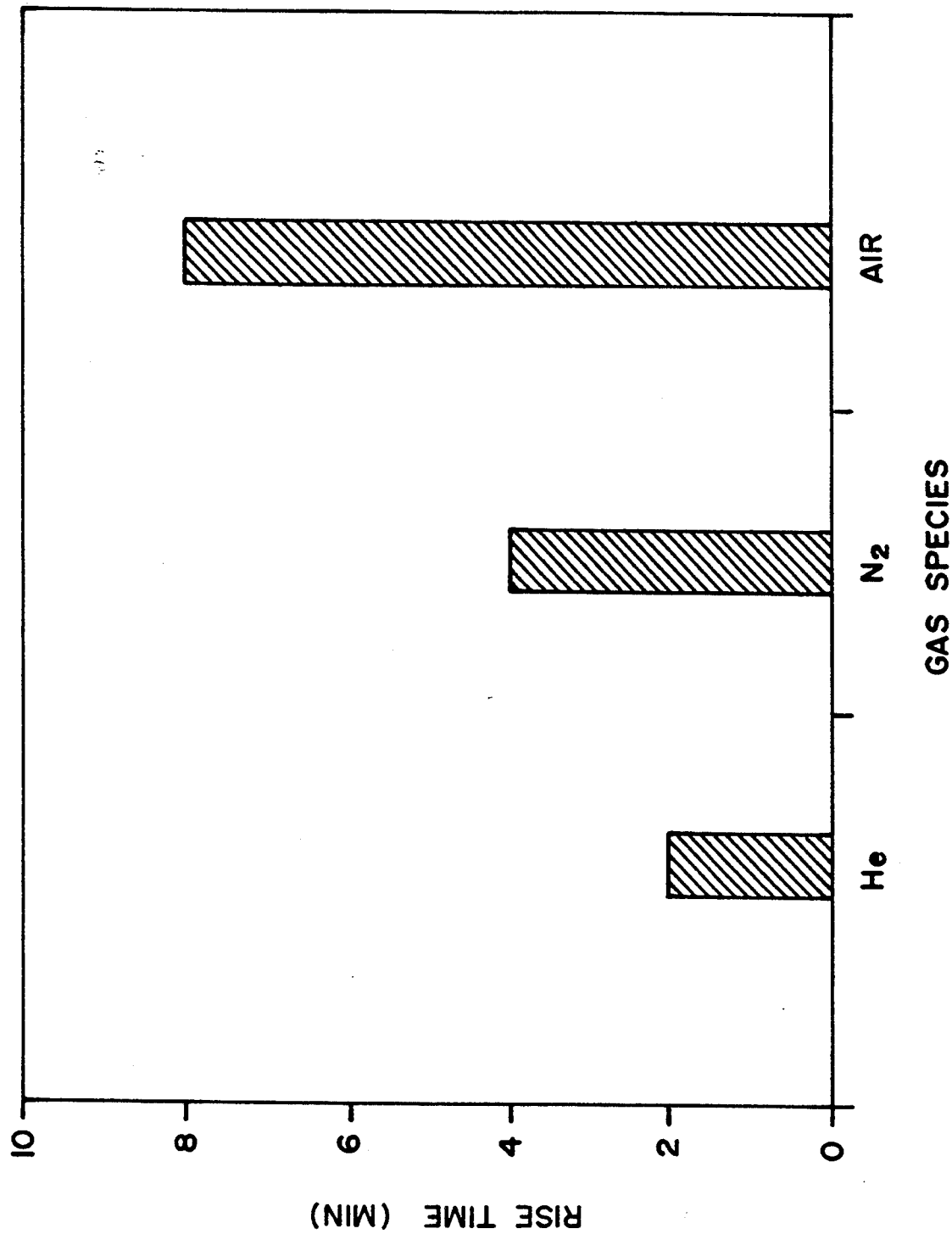
FIG. 5 is a bar diagram showing the response times of the sensor at room temperature in hydrogen in different atmospheres of helium, nitrogen and air.
Figure 6:
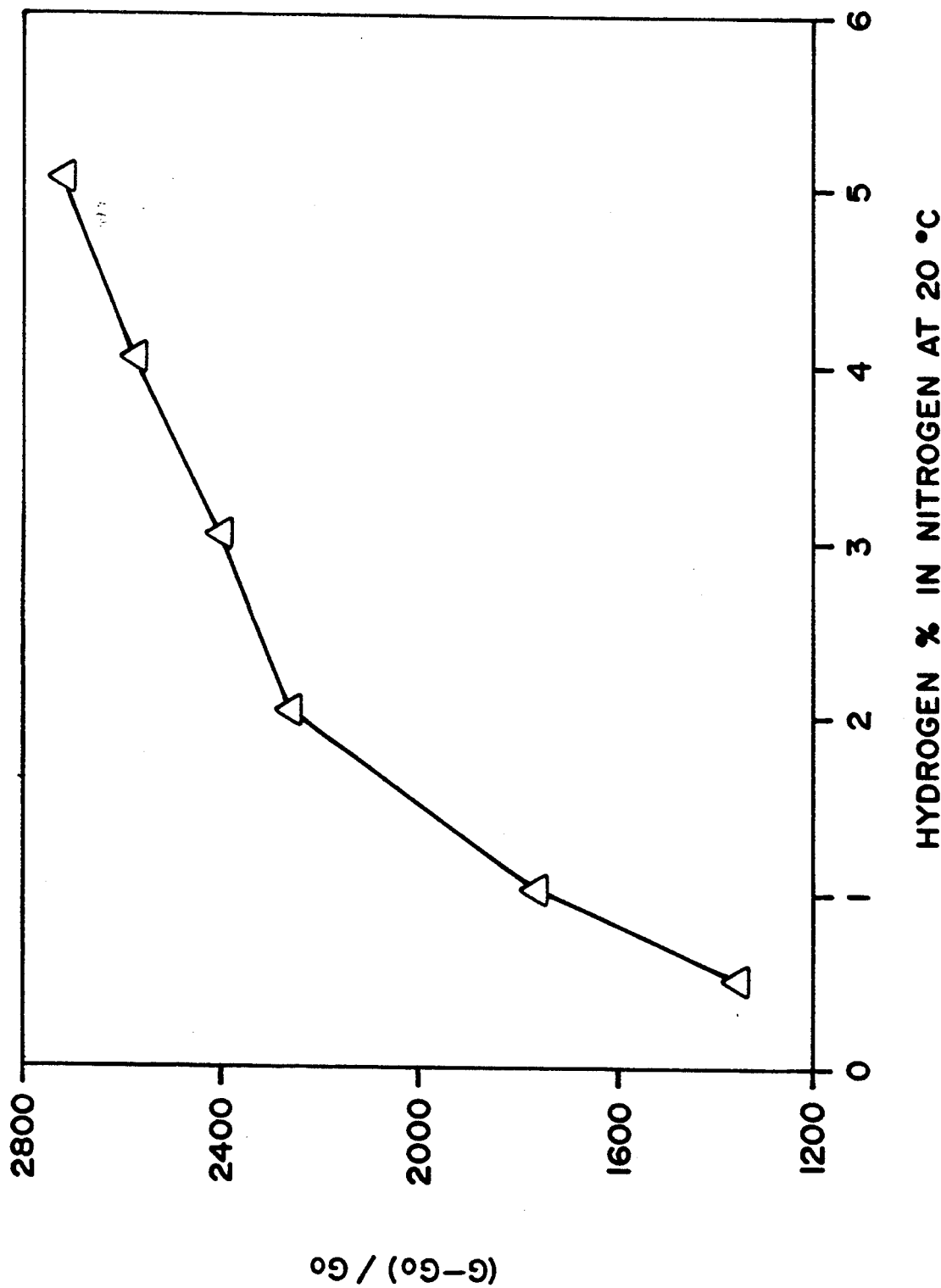
FIG. 6 is a graph showing the sensitivity of the sensor for different concentrations of hydrogen in nitrogen at 20° C.
Figure 7:
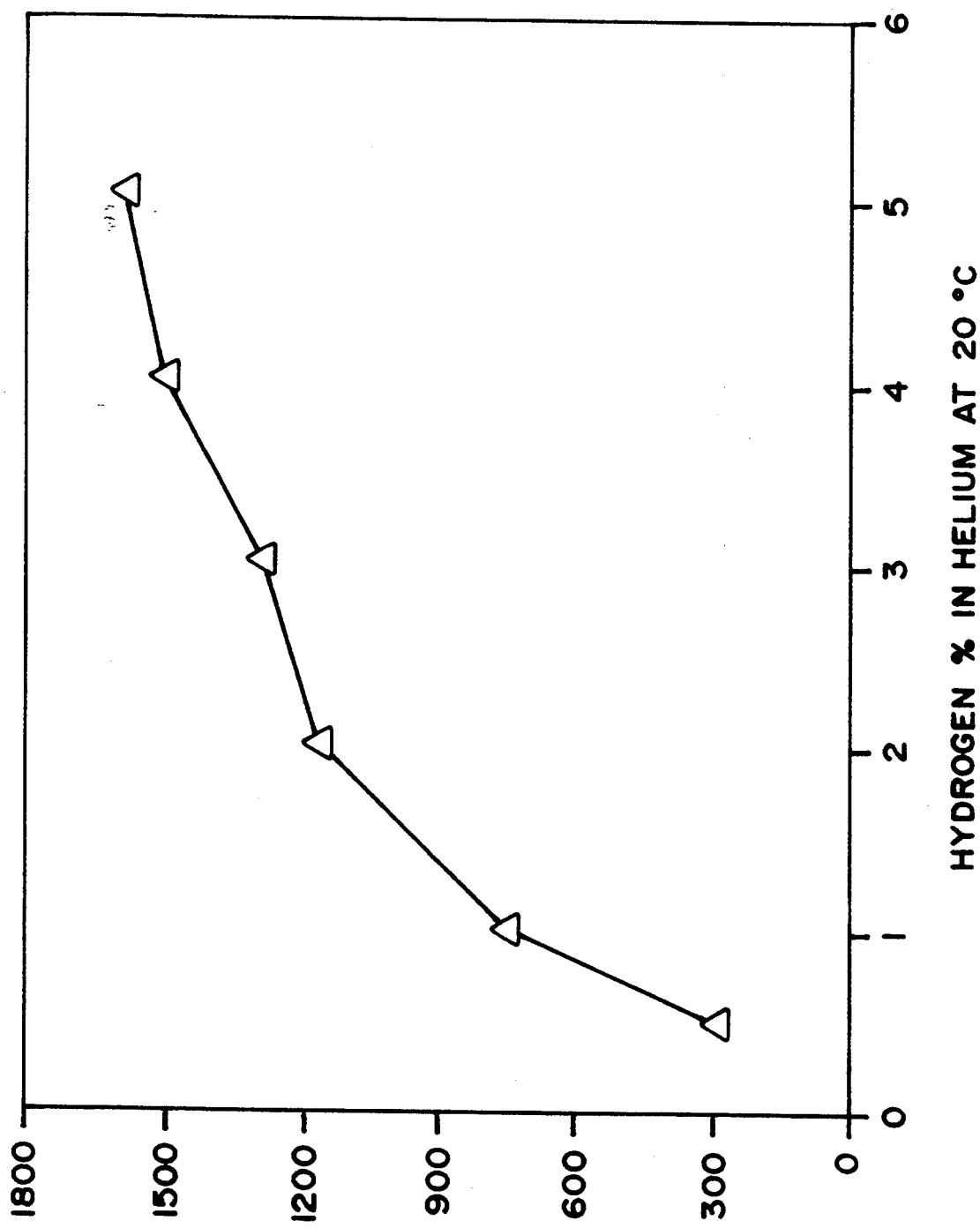
FIG. 7 is a graph showing the sensitivity of the sensor for different concentrations of hydrogen in helium at 20° C.

The sensitivity of the sensor depends not only on the concentration of the hydrogen gas, but on the atmosphere in which the hydrogen is sensed. The highest sensitivity for hydrogen is observed in He gas, next in $N_2$ and the lowest was observed in air. FIG. 5 shows the response time of the sensor in these three different atmospheres. The hydrogen concentration tested was 4%. This indicates that when the concentration of surface oxygen is reduced by replacing the air with, for example, helium molecules, the response is faster and the sensitivity to hydrogen is higher as seen in FIG. 7.

It should be noted however that the sensor is irreversible in a no-oxygen atmosphere. It must be exposed to oxygen to return to the high resistance baseline.

What is claimed is:

1. A sensor for reducing agents comprising:
   an insulating substrate;
   a pair of electrical contacts spaced-apart on the substrate;
   a film on the substrate between the contacts, the film having the formula $MO_z$ wherein M is selected from the group consisting of molybdenum, tungsten and titanium, O is oxygen and z is 3 when M is molybdenum or tungsten and 2 when M is titanium, the film being a plurality of single molecular thickness layers which are oriented so their basal planes are parallel.

2. A sensor as claimed in claim 1, wherein the film is impregnated with a metal selected from the group consisting of platinum, palladium and ruthenium.

3. A sensor as claimed in claim 1, wherein the film contains $MS_2$, wherein S is sulfur and the $MS_2$ is in the form of a plurality of single molecular thickness layers which are layered so their basal planes are parallel.

* * * * *